(12) United States Patent
Levy et al.

(10) Patent No.: US 6,277,886 B1
(45) Date of Patent: Aug. 21, 2001

(54) PHARMACEUTICAL COMPOSITIONS COMPRISING S-(–)-N-PROPARGYL-1-AMINOINDAN

(75) Inventors: Ruth Levy, Tel-Aviv; Moussa B. H. Youdim, Haif; John P. M. Finberg, Keryat Tivon; Sasson Cohen, Tel-Aviv; Jeff Sterling, Jerusalem, all of (IL)

(73) Assignees: Teva Pharmaceutical Industries, Ltd., Jerusalem (IL); Technion Research and Development Foundation, Ltd., Technion City (IL)

( * ) Notice: Subject to any disclaimer, the term of this patent is extended or adjusted under 35 U.S.C. 154(b) by 0 days.

(21) Appl. No.: 09/228,153

(22) Filed: Jan. 11, 1999

Related U.S. Application Data

(63) Continuation of application No. PCT/IL97/00205, filed on Jun. 20, 1997.

(30) Foreign Application Priority Data

Jul. 11, 1996 (IL) ........................................................ 118836

(51) Int. Cl.$^7$ .................................................. A61K 31/135
(52) U.S. Cl. ........................... 514/647; 514/878; 514/879; 514/903
(58) Field of Search ..................................... 514/647, 878, 514/879, 903

(56) References Cited

U.S. PATENT DOCUMENTS

| 3,513,244 | * | 5/1970 | Gittos et al. | .......................... 424/320 |
| 5,519,061 | * | 5/1996 | Youdim et al. | ...................... 514/647 |

FOREIGN PATENT DOCUMENTS

| 0436492 | 7/1991 | (EP) . |
| 0538134 | 4/1993 | (EP) . |
| 9518617 | 7/1995 | (WO) . |
| 9637199 | 11/1996 | (WO) . |
| 9712583 | 4/1997 | (WO) . |
| 9802152 | 1/1998 | (WO) . |

* cited by examiner

*Primary Examiner*—Frederick Krass
(74) *Attorney, Agent, or Firm*—John P. White; Cooper & Dunham LLP

(57) ABSTRACT

Pharmaceutical compositions for the treatment of a neurological disorder of neurotrauma or for improving memory in a patient comprising a therapeutically effective amount of S-(–)-N-proparygl-1-aminoindan or a pharmaceutically acceptable salt thereof as active ingredient, and a pharmaceutically active carrier. The pharmaceutical compositions are adapted, in particular for treating a neurological hypoxia or anoxia, neurodegenerative diseases. Parkinson's Disease, Alzheimer's Disease, neurotoxic injury, head trauma injury, spinal trauma injury or any other form of nerve damage.

21 Claims, 1 Drawing Sheet

PHARMACEUTICAL COMPOSITIONS COMPRISING S-(-)-N-PROPARGYL-1-AMINOINDAN

This application is a continuation of PCT International Application No. PCT/IL97/00205, filed Jun. 20, 1997, claiming priority of Israeli Patent Application No. 118836, filed Jul. 11, 1996, the contents of which are hereby incorporated in their entireties into the present application.

FIELD OF THE INVENTION

The present invention concerns the novel therapeutical use of S-(-)-N-propargyl-1-aminoindan and pharmaceutically acceptable salts thereof for the treatment of neurological disorders or neurotrauma and for improving memory in a patient.

As used herein, the term "neurotrauma" is meant to refer to damage caused to the central and/or peripheral nervous system as a result of ischemic damage such as a stroke, hypoxia or anoxia, neurodegenerative diseases, Parkinson's Disease, Alzheimer's Disease, neurotoxic injury, head trauma injury, spinal trauma injury or any other form of nerve damage.

BACKGROUND OF THE INVENTION

R(-) deprenyl (also known as L-deprenyl), N,α-dimethyl-N-2propenylphenethylamine) is a well-known inhibitor of the B-form of monoamine oxidase enzyme (hereinafter "MAO-B").

PCT International Application No. WO92/17169 describes the activity of R(-) deprenyl in maintaining, preventing the loss of, or recovering nerve growth function. This publication includes a list of deprenyl-like derivatives that are suggested to possess similar activities, althought no data is given in support of this contention. Included in the list is AGN-1135 which is racemic N=propargyl-1-aminoindan.

In a subsequent article Tatton, W. G. et al., *J. Neuroscience*, 13(9), pp. 4042–4053, (1993) report that the neuroprotective activity of deprenyl is limited to the R(-) enantiomer. The S(-) enantiomer was 2000 times less active in increasing the survival of axotomized immature rat facial mononeurons. Furthermore, it was demonstrated that neuroprotective activity is associated only with the R-enantiomers of propargyl derivatives that posses MAO-B inhibitory activity. Davis et al., *J. Neurochem.* Supplement 1, 64:S60, (1995) (recording the data presented by the same author at the Twenty-sixth Meeting of the American Society for Neuro-chemistry, held in Santa Monica, Calif., USA on Mar. 5–9, 1995) disclosed that in various models of neuroprotective activity, the R—' enantiomers of certain aliphatic N-methylpropargylamines that are selective inhibitors of MAO-B, were more effective in rescuing damaged neurons than their corresponding S-enantiomers.

The development of the work on deprenyl has led to the belief that the neuroprotective activity does not involve inhibition of MAO-B, because sub-inhibitory levels of R(-) deprenyl have been observed to prevent nerve cell death (Tatton, *Movement Disorders*, 8(1):S20–S30, (1993)). It has been proposed that R(-) deprenyl is perhaps dependent on interaction with a subtype of MAO-B that possesses extreme sensitivity to R(-) deprenyl.

Yu et al., *J. Neurosci*, 63, pp. 1820–1827, (1994) have assessed the activity of R(-)- and S(+)-deprenyl and several aliphatic propargylamine derivatives in reversing the noradrenaline depletion in rodents induced by the administration of N-(2-chloroethyl)-N-ethyl-2-bromobenzylamine (DSP-4). The end-point measured and described as an indication of "neuroprotective activity" was the percent restoration of noradrenaline as compared to untreated controls. In the results described, R(-) deprenyl and several of the higher N-aliphatically substituted propargylamines displayed "neuroprotective activity". S(+) deprenyl was described as acting like the known noradrenaline uptake inhibitor desipramine, having a far lower "neuroprotective activity" in comparison with R(-) deprenyl. In summary, S(+) deprenyl was shown to be a superior noradrenaline uptake inhibitor as compared to R(-) deprenyl, yet far inferior in the described measure of "neuro-protective activity".

European Patent 436,492 discloses that R(+) enantiomer of N-propargyl-1-aminoindan (hereinafter referred to as "R(+)PAL") as a selective irreversible inhibitor of MAO-B. Due to this specific activity R(+)PAI has also been proposed for use in the treatment of Parkinson's Disease, memory disorders, dementia (particularly of the Alzheimer's type) depression and hyperactive syndrome in children. U.S. Pat. Nos. 5,387,612, 5,453,446 and 5,457,133 relate to R(+)PAI and to methods of treating patients suffering from Parkinson's Disease comprising administering R(+)PAI to the patient. In these U.S. patents emphasis is placed on the superior MAO-B inhibitory activity of R(+)PAI as compared to its antipode, the S(-) enantiomer of N-propargyl-1-aminoindan (hereinafter referred to as "S(-)PAI"). In in vitro assays R(+)PAI was found to be nearly 7,000 times more active as an inhibitor of MAO-B than S(-)PAI. It was also found in these assays that, whereas R(+)PAI is more than 29 times more selective for MAO-B than MAO-A (the A-form of monoamine oxidase enzyme), S(-)PAI showed no preference to either substrate. This effect was also observed in both acute a chronic in vivo administration.

PCT International Application Publication No. WO95/11016 further disclosed that R(+)PAI is active as a "neuroprotective agent". The data therein describes its use in the prevention of NMDA induced cell death in rat cerebellum cells as well as in slowing neuronal degeneration when administered after crushing the rat optic nerve. No indication is given in this publication as regards the mechanism by which R(+)PAI may exert its "neuroprotective" effect.

The use of MAO inhibitors as neuronal rescue agents in clinical situations where neuronal survival is in jeopardy, might involve the important disadvantage resulting from their potential cardiovascular side-effects, alone or following drug-drug or drug-food interactions. These side-effects are attributed to partial or total inhibition of peripheral MAO-A, resulting in excessive concentrations of norepinephrine in the cardiovascular system (see for example, Physicians' Desk Reference 48th Edition, 1994, Medical Economics Data, Montvale, N.J., under Eldepryl). Selective MAO-B inhibitors such as R(-) deprenyl are less prone to compromise the cardiovascular system than the less specific agents such as pargyline or clorgyline, hence the former are probably the safer agents. However, the MAO subtype selectivity of these agents as determined under in vitro conditions tends to decrease dramatically when determined in vivo. Thus, the ratio to the in vitro $IC_{50}$ values of MAO-A/MAO-B for R(-) deprenyl has been reported by various authors as 400, 247, 360 and 16 (from a compilation by W. Paul and I. Szelenyi, in "Inhibitors of Monoamine Oxidase-B", I Szelnyi editor, Birkhauser, Basel, p. 353, 1993), suggesting a safety factor of about 100 or more. The recommended daily dose of R(-) deprenyl in human subjects is 10 mg, with 30–40 mg considered as the dose at which cardiovascular function could be compromised (Physicians' Desk Reference supra). Thus, the safety factor in clinical practice is about 3 to 4, as compared to about 400 in experimental systems in vitro.

There still exists, therefore, a need for a "neuroprotective agent" that, while being effective is free from the side-effects associated with hitherto known neuroprotectants of the MAO-B inhibitor type.

OBJECT OF THE INVENTION

It is thus an object of the present invention to provide a method and pharmaceutical compositions for treating CNS or PNS disorders, particularly those associated with neurotrauma, with an agent that possesses neuroprotective activity but does not display the peripheral side-effects associated with the known MAO-B inhibitors.

SUMMARY OF THE INVENTION

The present invention, in accordance with one aspect thereof provides a method of treating a patient suffering from a neurological disorder or neurotrauma comprising administering to said patient a therapeutically effective amount of (S)-N-propargyl-1-aminoindan or a pharmaceutically acceptable salt thereof.

The invention specifically provides a method of treating a subject afflicted with a neurodegenerative disease, a neurotoxic injury, brain ischemia or a stroke, which method comprises administering to the subject an amount of S(-)-N-propargyl-1-aminoindan or a pharmaceutically acceptable salt thereof.

The invention also specifically provides a method of treating a subject afflicted with neural injury following an episode of hypoxia or anoxia, head trauma injury of spinal trauma injury which method comprises administering to the subject of amount of S(-)-N-propargyl-1-aminoindan or a pharmaceutically acceptable salt thereof.

The present invention further provides a method of preventing nerve death in a subject which comprises administering to the subject an amount of S(-)-N-propargyl-1-aminoindan or the pharmaceutically acceptable salt thereof.

The present invention further provides a method of treating a subject afflicted with a memory disorder which comprises administering to the subject an amount of S(-)-N-propargyl-1-aminoindan or a pharmaceutically acceptable salt thereof effective to improve the memory in the subject.

In accordance with another aspect, the invention provides a pharmaceutical composition for the treatment of a neurological disorder or neurotrauma or for improving memory in a patient which comprises a therapeutically effective amount of S(-)-N-propargyl-a-aminoindan or a pharmaceutically acceptable salt thereof and a pharmaccutically acceptable carrier.

In accordance with yet another aspect of the present invention, there is provided S-(-)-N-propargyl-1-aminoindan or a pharmaceutically acceptable salt thereof for use as a medicament for the treatment of a neurological disorder or neurotrauma or for improving memory in a patient.

In accordance with yet another aspect of the present invention, there is provided the use of S-(-)-N-propargyl-1-aminoindan or a pharmaceutically acceptable salt thereof as active ingredient in the manufacture of medicaments for improving memory in a patient.

DETAILED DESCRIPTION OF THE INVENTION

S(-)-propargyl-1-aminoindan may be prepared as described in U.S. Pat. No. 5,457,133 and compositions may be prepared in a similar manner to those described in that patent.

in the practice of this invention, it is preferable that a pharmaceutically acceptable salt of S(-)-N-propargyl-1-aminoindan is used. Suitable pharmaceutically acceptable salts include, but are not limited to, the mesylate, maleate, fumarate, tartrate, hydrochloride, hydrobromide, esylate, p-toluene sulfornate, benzoate, acetate, phosphate and sulfate salts. Preferred are the hydrochloride, mesylate, esylate and sulfate salts of S(-)-N-propargyl-1-aminoindan. Most preferably, the pharmaceutically acceptable salt is the mesylate salt.

For the preparation of pharmaceutically acceptable acid addition salts of S(-)PAI, for free base can be reacted with the desired acids in the presence of a suitable solvent by conventional methods. Similarly, an acid addition salt may be converted to the free base form in the known manner.

As stated above, the invention provides, in accordance with one aspect thereof, a pharmaceutical composition which comprises a therapeutically effective amount of S(-)-N-propargyl-1-aminoindan or a pharmaceutically acceptable salt thereof and a pharmaceutically acceptable carrier. The "therapeutically effective amount" of the S(-)-N-propargyl-1-aminoindan or pharmaceutically acceptable salt thereof may be determined according to methods well known to those skilled in the art. These compositions may be prepared as medicaments to be administered orally, parenterally, rectally, or transdermally.

The preferred dosages of the active ingredient, i.e., S(-) PAI, in the above compositions are within the following ranges. For oral or suppository formulations, 0.1–100 mg per dosage unit may be taken daily, and preferably 1–10 mg per dosage unit is taken daily. For injectable formulations, 0.1–100 mg/ml per dosage unit may be taken daily, and preferably 1–10 mg/ml per dosage unit is taken daily.

These compositions may be used alone to treat the above-listed disorders, or alternatively, as an adjunct to the conventional treatments.

Suitable forms for oral administration include tablets, compressed or coated pills, dragees, sachets, hard or soft gelatin capsules, sublingual tablets, syrups and suspensions.

In one embodiment, the pharmaceutically acceptable carrier is a solid and the pharmaceutical composition is a tablet. The therapeutically effective amount of the active ingredient may be from about 0.1 mg to about 100 mg, preferable from about 1 mg to about 10 mg.

In an alternative embodiment, the pharmaceutically acceptable carrier is a liquid and the pharmaceutical composition is an injectable solution. The therapeutically effective amount of the active ingredient may be from about 0.1 mg/ml to about 100 mg/ml, preferably from about 1 mg/ml to about 10 mg/ml. In one embodiment, the dosage form is an infusion.

In a further alternative embodiment, the carrier is a gel and the pharmaceutical composition is a suppository.

For parenteral administration the invention provides ampoules or vials that include an aqueous or non-aqueous solution or emulsion of the active ingredient. For rectal administration there are provided suppositories with hydrophilic or hydrophobic vehicles. For topical application as ointments and transdermal delivery there are provided suitable delivery systems as known in the art.

The invention will be described in more detail in the following non-limiting Examples.

EXAMPLES

CHEMICAL EXAMPLES

Example 1

Di-(S-(−)-N-Propargyl-1-aminoindan) D-tartrate a) Racemic N-propargyl-1-aminoindan To a mixture of racemic 1-aminoindan (64 g), 15% aqueous sodium hydroxide solution (141 g), water (107 mL) and toluene (192 mL) there was added propargyl benzenesulfonate (94.3 g) during 20 minutes at ambient temperature. The resulting mixture was heater to 45° C. for 4 hours, at which time the pH was confirmed to be >12(45% sodium hydroxide added if necessary) and the phases were separated. To the organic phase water (64 mL) was added and the pH was adjusted to 2 with 33% aqueous sulfuric acid. The aqueous phase was separated, diluted with water and mixed with toluene. The pH was adjusted to 6 with 25% aqueous sodium hydroxide and the phases separated. The aqueous phase was extracted again with toluene, ensuring a pH=6. The combined organic layers were concentrated in vacuo to yield 51 g of crude racemic N-propargyl-1-aminoindan as a yellow oil.

b) Di-(S-(−)-N-propargyl-1-aminoindan) D-tartrate

To a solution of crude racemic N-propargyl-1-aminoindan (46.5 g) in isopropanol (157 mL) at reflux, was added a solution of D-tartaric acid (15.3 g) in water (28 mL). After 1 hour of reflux the mixture was slowly cooled to ambient temperature and the resulting precipitate was isolated by filtration with suction and washed with isopropanol. The crude di-(S-(−)-N propargyl-1-aminoindan) D-tartrate was recrystallized from 1 L of isopropanol containing 15% of water to yield 26.5 grams of the title compound: m.p. 175–177° C. $[\alpha]_D$ −34.3° (1.5, $H_2O$); Anal. cald. for $C_{25}H_{32}O_6N_2$ C, 68.26:H, 6.56;N,5.69; Found: C, 68.76; H, 6.57; N, 5.61;

Example 2

S-(−)-N-Propargyl-1-aminoindan mesylate

A solution of di-(S-(−)-N-propargyl-1-aminoindan) D-tartrate (15 g) from Example 1, and methanesulfonic acid (6 g) in isopropanol (150 ml) was heated to reflux for 30 minutes. The reaction mixture was allowed to cool to room temperature and the resulting precipitate isolated by suction filtration to yield the title compound (11.1 g) with m.p. 157° C., $[\alpha]_D$ −22°. Anal. calcd. for $C_{13}H_{17}NSO_3$: C, 58.43; H, 6.37; N, 5.24; S, 11.98; Found: C, 58.70; H, 6,39; N, 5.20; S, 11.82.

Example 3

S-(−)-N-Propargyl-1-aminoindan mesylate

To a solution of sodium hydroxide (4.8 g) in water (80 mL) was added di-S-(−)-N-propargyl-1-aminoindan) D-tartrate from Example 1 and toluene (80 mL). After stirring for 30 minutes, the mixture was filtered through Celite with suction and the organic layer was separated and washed with water. The organic phase was concentrated in vacuo, diluted with isopropanol and reconcentrated. The residue was dissolved in isopropanol (125 mL) and treated with methanesulfonic acid (11.5 g). The resulting mixture was heated to reflux for 30 minutes, filtered (Celite) and allowed to cool to ambient temperature. The resulting precipitate was collected by filtration and washed with isopropanol to yield the title compound with identical physical and chemical properties as the product of Example 2.

Example 4

S-(−)-N-Propargyl-1-aminoindan mesylate

The method of Example 1a was repeated except that S-(−)-1-aminoindan prepared according to Examples 76–80 of U.S. patent application Ser. No. 08/372,064 (filed Jan. 12, 1995) now abandoned, was used instead of racemic 1-aminoindan. The resulting yellow oil (30 grams) was dissolved in 180 ml of isopropanol, 17.7 grams of methanesulphonic acid were added and the resulting mixture heated to reflux and allowed to cool. The precipitate was isolated by filtration and recrystallized from isopropanol with activated charcoal to give the title compound with identical physical and chemical properties as the compound of Example 2.

Example 5

S-(−)-N-Propargyl-1-aminoindan hydrochloride 12.4 g of S-(−)-1-aminoindan and 12.9 g of potassium carbonate were added to 95 ml of acetonitrile. The resulting suspension was heated to 60° and 5.6 g of propargyl chloride were added dropwise. The mixture was stirred at 60° C. for 16 hours, whereafter most of the volatiles were removed by distillation in vacuo. The residue was partitioned between 10% aqueous sodium hydroxide and methylene chloride. The organic phase was dried and the solvent removed in vacuo. The residue was flash chromatographed on silica gel, eluting with 40% ethyl acetate/60% hexane. Fractions containing the free base of the title compound were combined and the solvent replaced by ether. The ethereal solution was treated with gaseous HCl and the resulting precipitate was isolated by suction filtration and recrystallized from isopropanol to yield 6.8 g of the title compound. The product exhibited $[\alpha]_D$ −30.3° (2% ethanol), m.p. 183–5° C.

BIOLOGICAL EXAMPLES

Example 1

Lack of inhibition of MAO activity in vivo by S(−) PAI mesylate

Rats (male Sprague-Dawley-derived) weighing 250±20 g were treated with one of the enantionmers or the racemic form of PAI by intraperitoneal injection (ip) or oral gavage (po), and decapitated 1h or 2h later respectively. Groups of three rates were used for each dose level of substance, and MAO activity determined in brain and liver using the general technique described in Example 19 of U.S. Pat. No. 5,387,612. The amount of protein in each incubation was determined using the Follin-Lowry method, and enzyme activity calculated as nmol of substrate metabolized per hour of incubation for each mg of protein. Activity of MAO in tissues from animals treated with the enantiomers or the racemic form of PAI was expressed as a percentage of the enzyme activity in a group of control animals administered vehicle (water for oral administration, 0.9% saline for ip injection).

Results

None of the dose levels used produced any obvious behavioral alterations. The doses producing 50%, inhibition of MAO-A and MAO-B ($IC_{50}$) were calculated from the inhibition curves, and are shown in Table 1. These data reflect the extremely low activity of S(−)PAI mesylate for inhibition of MAO-A and MAO-B, compared to the selectivity of R(+) PAI mesylate for MAO-B inhibition.

TABLE 1

IC-50 values (mg/kg) for Inhibition of MAO-A and MAO-B
by S(−)PAI mesylate, or R(+)PAI mesylate in rat brain and liver
following intraperitoneal injection (ip) or oral administration (po).

|  | MAO-A | | MAO-B | |
| --- | --- | --- | --- | --- |
|  | S(−)PAI mesylate | R(+)PAI mesylate | S(−)PAI mesylate | R(+)PAI mesylate |
| ip brain | >10 | 1.2 | >10 | 0.07 |
| ip liver | >10 | 5 | >10 | 0.06 |
| po brain | >10 | >5 | >10 | 0.17 |
| po liver | >10 | >5 | >10 | 0.05 |

Example 2

Neuroprotective effect of S(−)PAI in the hypobaric hypoxia model

The model used is analogous to the one described by M. Nakanishi et al., Life Sci. 13: 467–476 (1973); and by Y'Oshiro et al., J. Med. Chem. 34: 2014–2023 (1991). A group of 4 ICR male mice each weighing 20–25 g were placed in a 2.5 L glass chamber (A) at atmospheric pressure. Chamber A is connected to a 12 L chamber (B) through a valve which is initially pressure. Chamber A is connected to a 12 L chamber (B) through a valve which is initially closed. The air in chamber B was evacuated to a pressure of 100 mmHg. The valve between the two chambers was opened rapidly, whereupon the pressure in chamber A fell within 14 seconds to 200 mmHg. The survival time of the mice in chamber A was determined to a maximum hypobaric exposure of 15 minutes. Effect of drug pretreatment on survival is calculated as the percent of the survival time of the drug-treated group as compared to saline-injected or vehicle-injected group. Control groups were tested twice, before and after each experiment and consisted of 12 to 16 mice, 4 per group. Each tested group always consisted of 4 mice in order to ensure a constant residual volume of oxygen in all tests. Survival time range of control mice was 108–180 seconds. The effect of each dose of the test drug was determined in duplicate, using a total of 8 mice, 4 per group. All drugs were administered i.p. one hour prior to hypoxia. Positive reference drugs were sodium pentobarbital at a dose of 40 mg/kg, or diazepam at a dose of 10 mg.kg, given 0.5 hour prior to hypoxia. Results are shown in Table 2.

TABLE 2

Effect of drug-treatment on relative survival time of mice at
200 mmHg, as percent of corresponding control

| Agent | i.p dose mg/kg | % protection ± SD relative to control |
| --- | --- | --- |
| saline/vehicle | 0.5 ml | 100 |
| Diazepam | 10 | 430 ± 59, p < 0.001 |
|  | 5 | 249166, p < 0.05 |
| Pentobarbital | 40 | 446 ± 1.05, p < 0.001 |
|  | 20 | 325 ± 166, p <0.002 |
| R(−)Deprenyl | 100 | 102 ± 75, (ns) |
|  | 50 | 79 ± 23, (ns) |
|  | 10 | 97 ± 70, (ns) |
| (R)(−) PAI | 100 | 358 ± 179, p <0.001 |
| mesylate | 50 | 410 ± 151, p < 0.001 |
|  | 10 | 116 ± 47, (ns) |

TABLE 2-continued

Effect of drug-treatment on relative survival time of mice at
200 mmHg, as percent of corresponding control

| Agent | i.p dose mg/kg | % protection ± SD relative to control |
| --- | --- | --- |
| (S)(−)PAI | 100 | 390 ± 197, p < 0.002 |
| mesylate | 50 | 406 ± 247, p < 0.01 |
|  | 10 | 84 ± 47 (ns) |

Example 3

Locomotor activity and brain infarct size in male Wistar rats after middle cerebral artery occlusion (MCA-O) in the absence and presence of PAI enantiomers A modification of the procedure described by Tamura et. al., was used (Tamura A, Graham D, McCullch J, Teasdale G. H. (1981) J. Cereb. Blood Flow and Metab. 1;53–60). Male Wistar rats (Olac England-Jerusalem) weighing 300–400 g each, were anesthetized with a solution of Equitesine administered i.p. at a dose of 3 ml/kg. Equitesine consists of 13.5 ml sodium pentothal solution (60 mg/ml), 3.5 g chloral hydrate, 1.75 g $MgSO_4$, 33 ml propylene glycol, 8.3 ml absolute alcohol, made up to 83 ml with distilled water.

Surgery was performed with the use of high magnification operating microscope, model SMZ-2B, type 102 (Nikon, Japan). In order to expose the left middle cerebral artery, a cut was made in the temporal muscle. The tip of the coronoid process of mandible was excised as well and removed with a fine rongeur. Craniectomy was made with a dental drill at the junction between the median wall and the roof of the inferotemporal fossa.

The dura matter was opened carefully using a 27 gauge needle. The MCA was permanently occluded by microbipolar coagulation at low power setting, beginning 2–3 mm medial to the olfactory tract between its cortical branch to the rhinai cortex and the laterate striate arteries. After coagulation, the MCA was severed with microscissors and divided to ensure complete occlusion. Following this, the temporalis muscle was sutured and laid over the craniectomy site. The skin was closed with a running 3-0 silk suture. A sham craniectomy operation was performed on a parallel group of rats, but without cauterization of the MCA. During the entire surgical operation (20–25 min) in either group, body temperature was maintained at 37to 38° C. by means of a body-temperature regulator (Kyoristsu, Japan) consisting of a self-regulating heating pad connected to a rectal thermister. At 24 and 48 hours post surgery a neurological score was taken in order to assess the severity of the injury in the drug-treated rats with respect to their untreated controls. At 48 hours, the animals were anesthetized with Equitesine and the severity of the injury was visualized by 2, 3, 5-triphenyl tetrazoiium chloride (TTC) staining. The volume of brain tissue incurring damage following ischemia was determined.

Drugs were administered as an i.p. injection in 0.3–0.4 ml distilled water, according to the following schedule:

3 mg/kg within 30 min before surgery; 2 mg/kg 60 min after occlusion; 3 mg/kg within 20–24 hours after surgery.

After 48 hours of ischemia induced by permanent occlusion, morphometric measurement of infarct volume was performed as follows by TTC staining, TTC 1% in saline was prepared immediately before use and protected from exposure to light by aluminum foil wrap. MCA-O rats were deeply anestheized and a 23-gauge butterfly needle with an extended tubing and a 20 ml syringe was inserted into the ventricle via thoracotomy. The right atrium was incised to allow outflow of saline. Heparine 50 i.u. in saline was delivered until the perfusate wa bloodless. A 30-ml TTC-filled syringe was exchanged for the saline syringe and TTC was injected into the left ventricle at a rate of 5 ml/min. Both perfusate solutions were administered at 37.5° C. The brains were removed and immersed into 20 ml of 1% TTC contained in tightly closed glass vials. These were further placed for 2 hours in a water bath maintained at 37° C. The TTC solution was decanted, the brain removed, wiped dry and placed into 10% buffered formalin solution for 3 days.

to walk the beam in either direction reveals some motor incoordination, lack of balance and limb weakness.

Gait. Ability to restore normal position to either hind contralateral or fore contralateral limb when intentionally displaced while on a narrow beam.

Balance. Ability to grasp and balance on a narrow beam 2 cm wide.

Locomotor activity. Total movements over a period of 15 min in an automated activity cage.

Ratings assigned to each of the above parameters are given in Table 3.

TABLE 3

Neurological scores assigned to each of 10 parameters of posture and locomotion

| | Parameter | Score | |
|---|---|---|---|
| a. | Activity in home cage | normal = 0 | hypoactive = 1 |
| b. | Sedation | none = 0 | marked = 1 |
| c. | Piloerection | none = 0 | marked = 1 |
| d. | Extension of contralateral forelimb towards floor when lifted by tail | good = 0 | flexed limb = 1 |
| e. | Spread of contralateral hind limb when lifted by tail (trapezoid posture) | good = 0 | flexed limb = 1 |
| f. | Grasp rod with contralateral limb for 5–15 sec. when suspended by armpit | good = 0 | poor = 1 |
| g. | Walk on beam 5 cm wide | good = 0 | poor = 1 |
| h. | Restoration of contralateral hind and/or forelimb to original position when intentionally displaced | good = 0 | poor = 1 (one limb) 2 (two limbs) |
| i. | Grasping & balance on beam 2 cm wide | good = 0 | poor = 1 |
| j. | Motor activity with respect to control (15 min in activity cage) | 0–25% of control = 3 26–50% of control = 2 51–75% of control = 1 76–100% of control = 0 | |
| k. | Tendency to lean on contralateral side | 1 | |
| l. | Contralateral circling when pulled by tail | 1 | |
| m. | Contralateral circling spontaneous | 1 | |

Six coronal slices each 2 mm thick, 3, 5, 7, 9, 11 and 13 mm from the frontal pole were obtained with a brain matrix (Harvard Apparatus, South Natick, Mass.). Infarction areas were measured with a video imaging and analyzer from both sides of the coronal slices and expressed in $mm^2$. The volume of the infarcted region in $mm^3$ was calculated by taking the sum of the ischemic areas in all six slices. Infarct volumes are shown in Table 4 below.

Neurological Score

The neurological score consists of the sum total of a series of ratings assigned to the performance of specific locomotor activities in a given rat. The scale runs from 0 (fully normal rats) to 13 (fully incapacitated rats). Most parameters are rated as either 0 (normal), or 1 (incapacitated); others are graded. The following tests were used in the present study.

General observational tests; hypoactivity; sedation; piloerection.

Motor reflex. Rats were lifted by the tail about 15 cm above the floor. Normal rats assume a posture in which they extend both forelimbs towards the floor and spread the hind limbs to the sides in a trapeze-like manner. MCAO, when severe, causes consistent flexion of the contralateral limb.

Motor ability. This is seen as the ability to grasp a rod 1 cm in diameter by the contralateral limb for 5–15 sec when the rat is left hanging on the rod through the arm pit.

Motor coordination. Normal rats are able to walk up and down a beam, 5 cm wide placed at a moderate slant. Failure Results The neurological severity score (NSS) and infarct volume were both significantly lower in the S(−) PAI treated rats than in saline-treated rats, as shown in Table 4.

TABLE 4

Neurological severity score ± SEM and brain infarct size ± SEM in rats after permanent middle cerebral artery occlusion in the rat

| Parameter | S(−)PAI treated | saline treated | p value |
|---|---|---|---|
| Number of rats | 24 | 24 | |
| Mean NSS ± SEM after 24 hours | 6.5 ± 0.48 | 7.2 ± 0.36 | 0.0543 |
| Mean NSS ± SEM after 48 hours | 5.0 ± 0.41 | 6.6 ± 0.44 | 0.0114 |
| Mean infarct size ± SEM ($mm^3$) | 200 ± 13 | 240 ± 11.2 | 0.0259 |
| Percent improvement in NSS over saline treated at 48 hours | 24 | | |

Under similar operating conditions, treatment with R(+) PAI resulted in about a 20% improvement in neurological score severity. Thus, neuroprotection in this particular model of neuronal insult was afforded almost equally by both the R- and S-enantiomers of the corresponding N-propargyl-1-aminoindan.

Example 4

Lack of effect of S-(-)-PAI on reserpine induced ptosis in rats

Reserpine-induced ptosis and its reversal test. Reserpine causes depletion of catecholamine stores, especially norepinephrine. This effect in the live animal is manifested among other things, in ptosis. Drugs that can prevent or inhibit reserpine-induced ptosis act either directly as noradrenergic agonists, or indirectly by decreasing or preventing the metabolic elimination of endogenous norepinephrine. MAO inhibitors belong to the latter category.

Rats were premedicated with either saline, R(-)deprenyl or S(-)PAI i.p. and then, 2 hours later, were injected with reserpine 5 mg/kg i.p. The degree of ptosis was scored on a 0 to 4 scale, where 4 represents eyes completely open, and 0 represents eyes completely closed. The data shown in Table 5 are consistent with the premise that S(-)-PAI does not cause an increase in endogenous norepinephrine concentrations.

TABLE 5

Mean score of reserpine-induced ptosis (5 mg/kg i.p.) with and without premedication with MAO inhibitors. Scores; taken 2 hours following reserpine administration

| Agent | dose (mg/kg) | (n) | Mean score |
|---|---|---|---|
| saline | | 12 | 0.86 |
| R(-)Deprenyl | 5 | 3 | 1.3 |
| | 10 | 6 | 3.16 |
| S(-)PAI | 5 | 6 | 1.8 |
| | 10 | 6 | 2.5 |
| | 20 | 6 | 1.5 |

Example 5

Lack of pressor response of intravenous S(-)PAI in the anesthetized cat.

Cats were anesthetized with i.v. nembutal 25 mg/kg. Anesthesia was maintained by additional injections of nembutal, 5 mg/kg, as needed. The femoral artery was cannulated and connected to a Statham pressure transducer for blood pressure recordings on a Grass multichannel Polygraph. The femoral vein was cannulated for i.v. injection of drugs. The results are given in Table 6 and show that neither mean arterial blood pressure (MABP) nor heart rate (HR) were affected by intravenous S(-)PAI given in increasing doses up to a cumulative dose of 1 mg/kg and as long as 45–60 minutes after injection.

TABLE 6

Changes in mean arterial blood pressure and heart rate in the nembutal anesthetized cat 45–60 min after intravenous injection of S(-)PAI

| Dose | Change in MABP (mmHg) | Change in PR (beats/min) |
|---|---|---|
| 0.01 | 4 | -8 |
| 0.03 | 7 | -12 |
| 0.01 | -5 | -10 |
| 0.03 | 5 | 8 |
| 0.1 | -12 | 0 |
| 1.0 | 2 | -5 |

Example 6

Lack of effect of S(-)PAI on the pressor response to catecholamines in the cat MAO inhibitors usually potentiate the pressor response to catecholamines because they block their metabolic elimination by the enzyme MAO, especially subtype A. Cats treated with S(-)PAI as described in Example 5 were further challenged with each of the following pressor agents: Phenylephrine, tyramine and norephinephrine. In each case, there was no significant potentiation of the pressor response after pretreatment with S(-)PAI AT 1 mg/kg i.v. Results are given in Table 7.

TABLE 7

Pressor response to intravenous catecholamines in the anesthetized cat, before and after pretreatment with S(-)PAI, given as an i.v. injection of 1 mg/kg

| Agent & dose (µg/kg) | | Δ mean arterial pressure (mmHg) before S(-)PAI | Δ mean arterial pressure (mmHg) after S(-)PAI |
|---|---|---|---|
| norepinephrine | 0.02 | 8 | 12 |
| | 0.05 | 23 | 32 |
| | 0.10 | 31 | 23 |
| | 0.20 | 46 | 46 |
| phenylephrine | 0.20 | 9 | 2 |
| | 0.50 | 17 | 17 |
| | 1.0 | 21 | 17 |
| | 2.0 | 40 | 42 |
| tyramine | 2.0 | 11 | 3 |
| | 5.0 | 19 | 9 |
| | 10.0 | 26 | 28 |
| | 20.0 | 42 | 39 |

Example 7

Lack of cardiovascular effects of S(-)PAI in the conscious rat after acute oral administration.

A chronic indwelling catheter was implanted in the caudal artery under light anesthesia with averteen. The animals were allowed to recover and were tested 24 hours after implantation. The cathetar was connected to a Statham pressure transducer and blood pressure was recorded on a Grass multichannel Polygraph. During this period, the rat was kept in its home cage in order to minimize handling and undue manipulations known to affect blood pressure.

Two strains of rats were used: WKY rats and matching SHR (Spontaneously Hypertensive Rats) rats. WKY rats were from a local strain, weighing about 250 g each. In these, the maximum fluctuations of the mean arterial pressure (MAP) and heart rate (HR) were 8 mmHg and 49 beats per min, respectively, in the resting state.

SHR rats were purchased from Charles River breeders, England. The animals were allowed to acclimatize and recover from the journey and were used at the age of three months, in order to match their WKY controls. SHR hypertension develops gradually from the age of one month to the age of three months. At this stage, blood pressure is already elevated above normotensive levels.

S(-)PAI was administered in a volume of 10 ml/kg. Blood pressure and heart rate were then monitored for the duration of 45–60 minutes. Results are given in Table 8 and show that acute oral administration of S(-)PAI had no effect on either parameter in either strain of rats.

TABLE 8

Cardiovascular effects of S(–)PAI in conscious rats 45–60 min after oral administration

| Rat Strain | Dose | Change in MBAP (mmHg) | Change in HR (beats/min) |
|---|---|---|---|
| WKY | 1 | –9 | 70 |
|  |  | –24 | –130 |
|  | 2 | –6 | –20 |
|  |  | 9 | 70 |
|  | 5 | 0 | 0 |
|  |  | 0 | 0 |
|  | 10 | 0 | 0 |
|  | 20 | 0 | 0 |
|  |  | –12 | 0 |
| SHR | 1 | –16 | –30 |
|  | 2 | –12 | 0 |
|  | 5 | 13 | 0 |
|  |  | –6 | –40 |
|  | 10 | 4 | 0 |

Example 8

Lack of effect of S(–)PAI on systolic blood pressure in SHR rats after chronic oral administration at 2 mg/kg/day.

Spontaneously hypertensive rats, three month-old, were used. Each rat was given a daily dose of 2 mg/kg S(–)PAI in tap water 10 ml/kg. Controls received an equivalent volume of tap water. Treatment lasted 14 days. During this period, systolic blood pressure was monitored on days 0, 4, 7 and 11, using a tail-cuff procedure. On day 14, systolic blood pressure was determined using the indwelling catheter procedure described in Example 7. The results are given in Tables 9 and 10. Chronic oral treatment with S(–)PAI at 2 mg/kg/day had no effect on the intraindividual and interindividual profile of systolic blood pressure and heart rate.

TABLE 9

Effect of S(–)PAI (2 mg/kg p.o.) on systolic blood pressure and heart rate measured by tail cuff in SHR rats over a 2 week period.

|  | Day of Treatment | Change in Mean Systolic Blood Pressure (mmHg) | Change in Heart rate (beats/min) |
|---|---|---|---|
| TAP WATER | 0 | 169.55 ± 7.73 | 374.09 ± 7.17 |
|  | 4 | 177.82 ± 9.08 | 403 ± 23.3 |
|  | 7 | 177.67 ± 10.21 | 392.67 ± 24.66 |
|  | 11 | 178 ± 8.65 | 371.25 ± 27.22 |
| S(–)PAI | 0 | 166.88 ± 6.11 | 404.13 ± 32.86 |
|  | 4 | 168.5 ± 12.8 | 394.5 ± 37.43 |
|  | 7 | 172.13 ± 14.62 | 394.38 ± 24.47 |
|  | 11 | 167.43 ± 14.23 | 408 ± 40.04 |

TABLE 10

Cardiovascular effect of 2-week chronic oral treatment with S(–)PAI in SHR rats measured directly by an implanted catheter.

|  | Mean arterial blood pressure | Systolic blood pressure | Heart rate |
|---|---|---|---|
| TAP WATER | 107.65 ± 9.59 | 138.37 ± 13.41 | 404.55 ± 49.82 |
| S(–)PAI | 107.88 ± 5.35 | 140.79 ± 6.55 | 366.11 ± 34.99 |

Example 9

Lack of effect of S(–)PAI on body weight in SHR rats after chronic oral dosing at 2 mg/kg/day.

The rats used in Example 8 above, were additionally monitored for weight gain/loss as an additional marker for the rate of food consumption MAO inhibitors usually elevate central catechoiamines which may depress appetite. Chronic treatment with S(–)PAI at 2 mg/kg/day had no effect on body weight throughout 14 days of treatment. Results are given in Table 11.

TABLE 11

Effect on SHR rat body weight after 2 week chronic oral treatment with S(–)PAI.

|  | Day | Weight (g) |
|---|---|---|
| TAP WATER | 0 | 317 ± 32.64 |
|  | 7 | 302.22 ± 35.17 |
|  | 14 | 312.89 |
| S(–)PAI | 0 | 294.13 ± 32.06 |
|  | 7 | 292.25 ± 28.47 |
|  | 14 | 307.33 ± 24.13 |

Summary

Examples 4–9 show that S(–)PAI has minimal or no effect on several MAO mediated effects.

Example 10

Effect of S(–)PAI following closed head injury (CHI) in mice

The procedure for closed head injury followed was as described for rats in Shohami et al. (J Neurotrauma (1993) 10(2) 109–119) with changes as described.

Animals: Male Sabra mice (Hebrew University strain) weighing 34–40 g were used. They were housed in groups of 10 per cage, in a 12 hr:12 hr. light:dark cycle. Food and water were provided ad libitium.

Trauma was induced under anaesthesia. A longitudinal incision was performed in the skin covering the skull and the skin retracted to expose the skull. The head was fixed manually at the lower plane of the impact apparatus. A weight of 333 g was delivered by an electric device from a distance of 3 cm to the left hemisphere, 1–2 mm lateral to the midline in the midcoronal plane. S-PAI was injected sub-cutaneously (1 mg/kg) once 15 min. after CHI.

Assessment of Motor Function

Motor function and reflexes were evaluated in the injured mice at different times after closed head injury (CHI) using a neurological severity score (NSS*) as shown in Table 12 below, which is modified from that described for rats. One point was awarded for the lack of a tested reflex or for the inability to perform the task outline in the Table. The maximal score that can be reached at 1 hour post-CHI is 25 points and at later times, 21 points. The difference in NSS at 1 hr. and at any other time reflects the spontaneous recovery, and is referred to as ΔNSS. A score of 15–19 at 1 hr denotes severe injury, 11–14 denotes moderate injury and less than 10 denotes mild injury.

*The NSS assessed in this Example is different from that in Example 3, both in the parameters assessed and in the scoring system.

TABLE 12

Neurological Severity Score for mice after Closed Head Injury

| Parameter | Points at 1 hour post-CHI | Points at any other time |
|---|---|---|
| Inability to exit from a circle (30 cm diameter) when left in its center | | |
| for 30 min | 1 | |
| for 60 min | 1 | |
| for >60 min | 1 | 1 |
| Loss of righting reflex | | |
| for 10 second | 1 | |
| for 20 seconds | 1 | |
| for >30 seconds | 1 | 1 |
| Hemiplegia - inability of mouse to resist forced changes in position | 1 | 1 |
| Flexion of hind limb when lifted by tail | 1 | 1 |
| Inability to walk straight when placed on the floor | 1 | 1 |
| Reflexes | | |
| Pinna reflex | 1 | 1 |
| Corneal reflex | 1 | 1 |
| Startle reflex | 1 | 1 |
| Clinical grade | | |
| Loss of seeking behavior | 1 | 1 |
| Prostration | 1 | 1 |
| Loss of reflexes | | |
| Left forelimb | 1 | 1 |
| Right forelimb | 1 | 1 |
| Left hindlimb | 1 | 1 |
| Right hindlimb | 1 | 1 |
| Functional test | | |
| Failure in beam balancing task (0.5 cm wide) | | |
| for 20 seconds | 1 | 1 |
| for 40 seconds | 1 | 1 |
| for >60 seconds | 1 | 1 |
| Failure in round stick balancing task (0.5 cm in diameter | | |
| for 10 seconds | 1 | 1 |
| Failure in beam walking task | | |
| 3 cm wide | 1 | 1 |
| 2 cm wide | 1 | 1 |
| 1 cm wide | 1 | 1 |
| Maximum Points | 25 | 21 |

Assessment of Reference Memory

Morris Water Maze Test: the water maze consists of a circular aluminium pool, 1 m in diameter and 60 cm in depth, filled with water to a depth of 17.5 cm. The hidden goal platform is a glass vessel (15 cm diameter ×16.5 cm height) placed upside down at a fixed location in the pool, 1 cm below the surface of the water. The water temperature is maintained at 24° C. and the pool is always placed in the same position in the room to provide the same extra-maze cues. Prior to CHI, mice were given 3 trials per day for 5 consecutive days to establish a baseline performance—measured as the latency to find the platform from the same start location. Commencing 24 hr. after CHI mice were retested daily for 2 weeks in 3 trials per day.

Results
Assessment of Motor Function

TABLE 13

Change in Neurological Severity Score after Closed Head Injury in Mice

| Drug/dose | N | $\Delta$ NSS, 24 hr post-CHI | $\Delta$ NSS, 7 days post-CHI | $\Delta$ NSS, 14 days post-CHI |
|---|---|---|---|---|
| Saline, 1 ml/kg | 51 | 4.75 ± 0.17 | 5.83 ± 0.36 | 5.96 ± 0.4 |
| S(−)PAI, 1 mg/kg | 15 | 5.06 ± 0.25 | 7.19 ± 0.28 | 7.88 ± 0.36 |

BRIEF DESCRIPTION OF THE DRAWING

Assessment of Reference Memory

Figure 1:
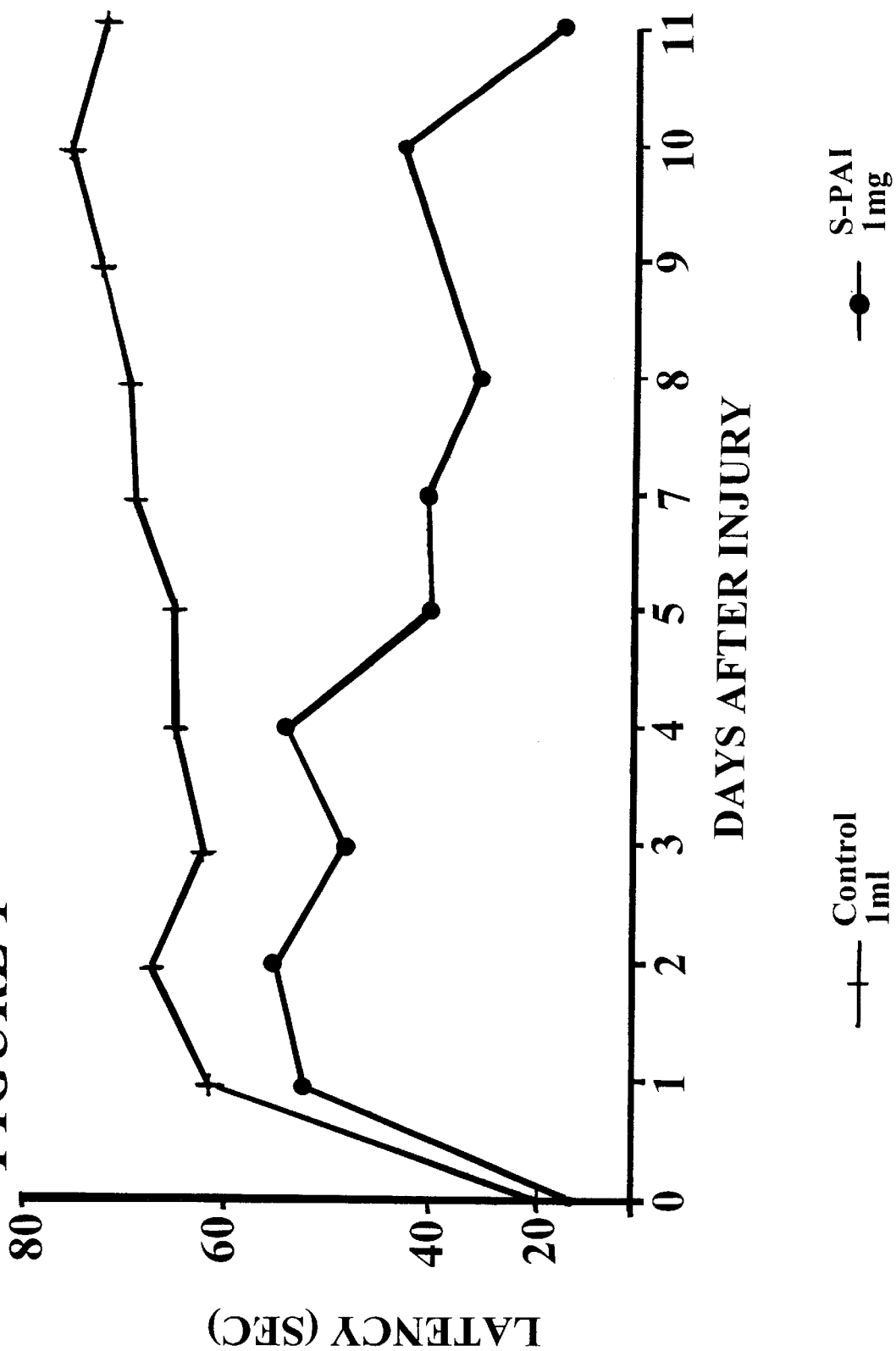
FIG. 1 shows the reduction in latency for mice treated with S(−)PAI compared to saline treated controls after CHI. It appears that immediately post-CHI mice forget the location of the goal. Memory is enhanced following treatment with S(−)PAI, as compared to saline treated mice.

What is claimed is:

1. A method of treating a subject suffering from neurotrauma comprising administering to the subject a composition consisting essentially of a therapeutically effective amount of (S)-(−)-N-propargyl-1-aminoindan or a pharmaceutically acceptable salt thereof.

2. The method of claim 1, wherein the subject is a human.

3. The method of claim 1, wherein the neurotrauma is a result of a neurodegenerative disease.

4. The method of claim 1, wherein the neurotrauma is a result of a neurotoxic injury.

5. The method of claim 1, wherein the neurotrauma is a result of brain ischemia.

6. The method of claim 1, wherein the neurotrauma is a result of a stroke.

7. The method of claim 1, wherein the neurotrauma is a result of an episode of hypoxia or anoxia.

8. The method of claim 1, wherein the neurotrauma is a result of a head trauma injury.

9. The method of claim 1, wherein the neurotrauma is a result of a spinal trauma injury.

10. The method of claim 1, wherein the neurotrauma is a result of Parkinson's Disease.

11. The method of claim 1, wherein the neurotrauma is a result of Alzheimer's Disease.

12. The method of claim 1, wherein the administration is oral, rectal, intra-venous, transdermal or parenteral administration.

13. The method of claim 1, wherein the therapeutically effective amount is from about 1 mg to about 1000 mg.

14. The method of claim 1, wherein the therapeutically effective amount is from about 10 mg to about 100 mg.

15. The method of claim 1, wherein the pharmaceutically acceptable salt is the hydrochloride, mesylate, esylate or sulfate salt of S-(−)-N-propargyl-1-aminoindan.

16. A method for preventing nerve death in a patient which comprising administering to the patient a composition consisting essentially of a therapeutically effective amount of (S)-(−)-N-propargyl-1-aminoindan or a pharmaceutically acceptable salt thereof.

17. A method of improving memory of a patient afflicted with a memory disorder which comprising administering to the patient a composition consisting essentially of a therapeutically effective amount of (S)-(−)-N-propargyl-1-aminoindan or a pharmaceutically acceptable salt thereof.

18. The method of claim 17, wherein the administration is oral, rectal, intra-venous, transdermal or parenteral administration.

19. The method of claim 17, wherein the therapeutically effective amount is from about 1 mg to about 1000 mg.

20. The method of claim 17, wherein the therapeutically effective amount is from about 10 mg to about 100 mg.

21. The method of claim 17, wherein the pharmaceutically acceptable salt is the hydrochloride, mesylate, esylate or sulfate salt of S-(−)-N-propargyl-1-aminoindan.

* * * * *